United States Patent [19]

Elgas

[11] Patent Number: 5,297,433
[45] Date of Patent: Mar. 29, 1994

[54] EXPANSION-CHAMBER/VIAL SPARGER VESSEL

[76] Inventor: David H. Elgas, 4886 Cannington Dr., San Diego, Calif. 92117

[21] Appl. No.: 845,999

[22] Filed: Mar. 4, 1992

[51] Int. Cl.[5] .................... G01N 30/00; G01N 33/18
[52] U.S. Cl. ................................ 73/864.85; 73/64.56; 73/23.41; 73/19.1
[58] Field of Search ................ 422/99, 100, 102; 73/61.44, 19.1, 19.01, 61.55, 61.59, 64.56, 23.41, 23.42, 864.91, 864.85

[56] References Cited

U.S. PATENT DOCUMENTS

| | | | |
|---|---|---|---|
| 3,249,403 | 5/1966 | Bochinski et al. | 73/864.85 |
| 3,713,629 | 1/1973 | Rieter | 261/112.1 |
| 4,036,704 | 7/1977 | Takata | 73/61.55 |
| 4,558,603 | 12/1985 | Chlosta et al. | 73/864.85 |
| 4,738,827 | 4/1988 | Pierotti | 73/864.91 |
| 4,758,408 | 7/1988 | Krawetz et al. | 73/19.01 |
| 4,838,098 | 6/1989 | Barney | 73/19.1 |
| 5,012,845 | 5/1991 | Averette | 422/103 |
| 5,062,292 | 11/1991 | Kanba et al. | 73/64.56 |
| 5,065,614 | 11/1991 | Hartman et al. | 73/23.41 |
| 5,080,868 | 1/1992 | Elgas | 422/99 |

Primary Examiner—Hezron E. Williams
Assistant Examiner—G. Dombroske
Attorney, Agent, or Firm—Calif Kip Tervo; 10

[57] ABSTRACT

In its simplest sense the invention is an expansion chamber device that allows a sample to be purged and trapped for analysis without removal of the sample from the common field sample vial (VOA vial) storing the sample. The expansion chamber generally comprises an expansion chamber tube of transparent material having a top end adapted for gas tight fit in a compression fitting of a host purge and trap instrument, a bottom end including an external flange, and a central passage for fluid communication between a sample vial top opening and a host purge and trap instrument. A connector cap has a bottom end having internal threads for mating with external threads on a sample vial and a top end having an internal flange for bearing down on the expansion chamber tube bottom end external flange. An inert gasket forms a positive pressure seal between the expansion chamber tube bottom end and the sample vial. In an exemplary embodiment, the expansion chamber tube bottom end further includes a tail piece that fits just inside a sample vial top end opening, and the expansion chamber tube internal passage includes surface modifications, such as a plurality of protrusions, for breaking up bubbles.

13 Claims, 1 Drawing Sheet

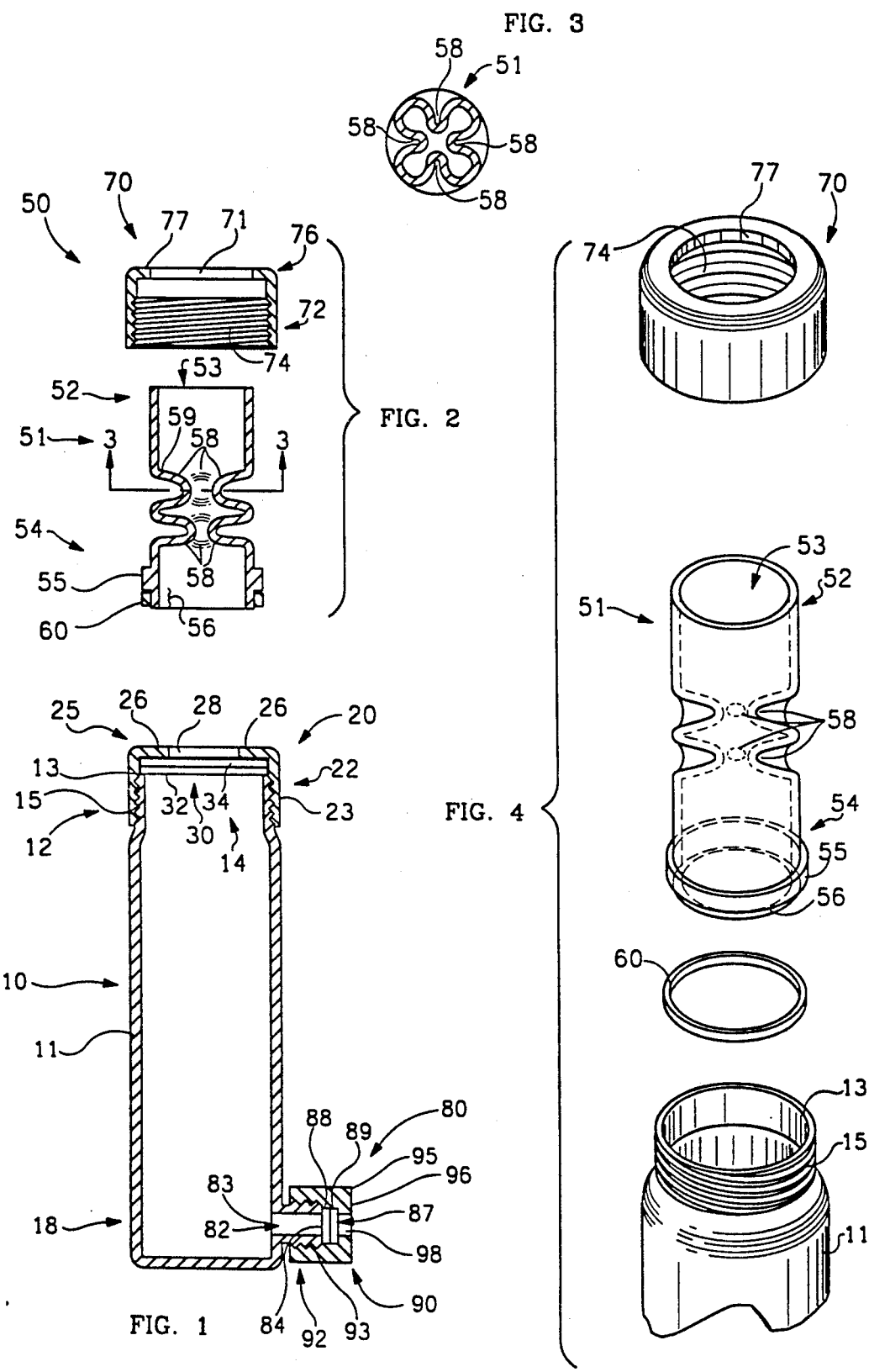

EXPANSION-CHAMBER/VIAL SPARGER VESSEL

BACKGROUND OF THE INVENTION

1. Field of the Invention

This invention relates in general to testing samples, e.g. water, for contaminants using a purge and trap instrument and more specifically involves a device that allows testing without removal of the sample from the volatile organic analysis vial in which the sample was field-collected.

2. Background of the Invention

It is often desirable to determine the presence and nature of volatile organic compounds, such as contaminants, in water, soil, and sludge. Typically, field samples are collected in glass bottles or vials. A common field sample collection bottle, called a volatile organic analysis (VOA) vial, is shown in cross-sectional view in FIG. 1 of the drawing and is denoted generally as 10. (Note: Vial 10 shown is common except for the spiking port, denoted generally as 80, which will be described in the Detailed Description.) VOA vial 10 generally includes a glass jar 11, a septum 30, and a cap 20. Glass jar 11, commonly of 40 cc or greater, has a top end 12 terminating in a rim 13 surrounding top opening 14. VOA vial top end 12 includes external threads 15 for attachment of cap 20. Cap 20 has a lower end 22 having internal threads 23 for attachment to vial threads 15. Cap top 25 includes an inward flange 26 surrounding bore 28. Septum 30 is a flexible disk that seals between cap flange 26 and vial rim 13 and covers vial top opening 14 to contain the test sample. Preferably, septum 30 is made of inert resilient material that will not interact with the sample, such as an inert elastomer or an elastomer encapsulated in an inert material, such as a solid fluorocarbon such as teflon. A commonly available septum has a bottom layer 32 of teflon, for contacting the sample and a top layer 34 of elastomer for elasticity and resiliency.

VOA vial 10 is completely filled in the field with liquid sample and capped with septum 30 and cap 20 to assure a gas tight fit. No headspace, i.e. air space, is left in the vial because volatiles in the sample would exit into the headspace and be lost upon opening the vial. Septum 30 is flexible and may move inward or expand outward through cap bore 28 to accommodate contractions and expansions of the sample.

The general testing method, called "purge and trap" requires placing a portion of the sample in a special sparging vessel. Sparging vessels typically hold up to 25 cc. After testing, the inexpensive and contaminated VOA vial containing any remaining sample is typically discarded. The test instrument passes high purity gas bubbles through the sample. The high purity gas bubbles collect the organic vapor and carry it to an absorption tube that concentrates the vapor for subsequent thermal desorption and analysis by gas chromatography or spectrum analysis.

Among other requirements, the special sparging vessels must contain an expansion chamber and must form a gas tight seal with the host purge and trap instrument. An expansion chamber is necessary to prevent contamination of the host instrument from liquids, either in the form of liquid, aerosol mist or foam, entering the instrument. Some samples will foam and bubble easily. Liquid entering the instrument contaminates the instrument which then requires many hours to clean out. Also, liquids entering the instrument may cause thousands of dollars of damage to the instrument. For this reason, it is preferable that the expansion chamber be visible to the user and be made of transparent material so that the user can watch for formation of foam and passage of liquid toward the host instrument. A gas tight seal between the sparge vessel and instrument for up to positive pressures of 20 psig is necessary to prevent any purged gas from escaping. Common commercial purge and trap analytical instruments include a pressure fitting that attaches to the output tube of the special sparging vessel with such a gas tight seal.

Testing requirements are becoming ever more stringent. Mercury and lead contaminants are to be measured in parts per billion. This necessitates testing larger samples and exacerbates some problems in the above-described standard.

One problem of the conventional method is that volatiles can be lost each time the sample or a part of the sample is transferred. Another problem is that the special sparging vessels are expensive and, therefore, are commonly re-used. Re-use of sparging vessels requires cleaning after each use and, of course, introduces doubts as to results obtained from future use of a re-used vessels.

Therefore, the applicant has concluded that it would be desirable to have an expansion chamber device that would connect to a common purge and trap compression fitting and allow the common field sampling VOA vial to be used as the sparging vessel. In this way, no volatiles would be lost due to transfer and no costly vessels are discarded or cleaned.

It is further desirable that the device include means for abating the foaming and bubbling problem.

Of course, it is very desirable that the device achieve these effects without adding any major drawbacks to the sparging operation.

Immediately following each purge and trap analysis it is desirable to test the performance of the instrument to determine the validity of the test results. One method of testing the instrument is to "spike" the sample, i.e. inject a known amount of volatile into the sample and analyze the recovered output.

Therefore, it would be additionally desirable if the field sample bottle includes means for spiking the sample.

SUMMARY OF THE INVENTION

In its simplest sense the invention is an expansion chamber device that allows a sample to be purged and trapped without removal of the sample from the common field sample vial storing the sample. The expansion chamber generally comprises an expansion chamber tube of transparent material having a top end adapted for gas tight fit in a compression fitting of a host purge and trap instrument, a bottom end including an external flange, and a central passage for fluid communication between a sample vial top opening and a host purge and trap instrument. A connector cap has a bottom end having internal threads for mating with external threads on a sample vial and a top end having an internal flange for bearing down on the expansion chamber tube bottom end external flange. An inert gasket forms a positive pressure seal between the expansion chamber tube bottom end and the sample vial. In an exemplary embodiment, the expansion chamber tube bottom end further includes a tail piece that fits just inside a sample vial top end opening, and the expansion chamber tube internal passage includes surface modifications, such as a plurality of protrusions, for breaking up bubbles.

Other features and many attendant advantages of the invention will become more apparent upon a reading of the following detailed description together with the drawings in which like reference numerals refer to like parts throughout.

BRIEF DESCRIPTION OF THE DRAWING

FIG. 1 is a cross sectional view of a typical VOA vial but with the addition of a spiking port.

FIG. 2 is an exploded cross sectional view of a preferred embodiment of the expansion chamber sparger assembly of invention.

FIG. 3 is a sectional view of anti-foam protrusions within the expansion chamber tube taken on line 3—3 of FIG. 2.

FIG. 4 is an enlarged exploded perspective view of an expansion-chamber and vial sparging vessel.

DETAILED DESCRIPTION OF THE INVENTION

With reference again to FIG. 1 of the drawing, there is shown a common organic analysis vial (VOA vial) 10 such as is filled with a sample taken in the field. Please refer to the Background of the Invention section above for a detailed description of vial 10. To construct the vial/expansion-chamber sparger of the invention, cap 20 and septum 30 are removed from vial 10 leaving jar 11 full of sample.

FIG. 2 is an exploded cross sectional view of a preferred embodiment of the expansion chamber assembly, denoted generally as 50, for attachment to the full sample jar 11. Expansion chamber assembly 50 generally comprises an expansion chamber tube, denoted generally as 51, a sealing means, such as O-ring gasket 60, and a connector 70.

Expansion chamber tube 51 is preferably made of transparent material, such as glass. Amber glass can be used for photosensitive samples. Tube 51 has a top end 52 adapted for gas tight coupling with a compression fitting of a host purge and trap instrument. This typically requires an tube with a circular outside diameter of 0.630 inches. Tube 51 has a bottom end 54 including a sealing surface, such as outward circular flange 55, and a tail piece 56. Tail piece 56 is adapted to fit snugly just inside top opening 14 of jar 11. Expansion chamber tube 51 has an internal volume sufficient to act as an expansion chamber for the purge gas and volatiles it collects from the sample. This is critical to prevent liquid from entering the host purge and trap instrument.

O-ring gasket 60 is preferably of inert resilient material, such as an inert elastomer or an elastomer encapsulated in an inert material, such as a solid fluorocarbon such as teflon. Gasket 60 seals between flange 55 and jar rim 13.

Connector 70 provides means for joining expansion chamber 51 to jar 11. Connector 70 is generally a hollow cylinder having a central passage 71 large enough to fit over expansion chamber tube top end 52 and a bottom end 72 having internal threads 74 for threaded coupling with sample jar external threads 23 and having a top end 76 having an inward facing flange 77 for bearing down on expansion chamber tube flange 55 and thereby retaining expansion chamber tube 51 to jar 11 and compressing gasket 60 into a sealing relationship between jar rim 13 and flange 55. Connector 70 may be made of any suitable material, such as plastic or metal.

Because of the small width W of gasket 60, gasket 60 has a tendency to slip off of rim 13 upon tightening down connector 70. Therefore, gasket 60 has been found to work best if its inside diameter fits tightly around tail piece 56. This arrangement also holds the gasket in position during assembly.

Also, in the preferred embodiment shown having tail piece 56, it has been found to be not so important if gasket 60 is of such extremely inert material as teflon, because gasket 60 is only slightly and remotely exposed to the sample.

Preferably, expansion chamber tube 51 includes means, such as internal surface modifications, such as a plurality of protrusions 58, to aid in preventing liquid from entering the host instrument.

FIG. 3 is a cross sectional view of the anti-foam protrusions 58 taken on line 3—3 of FIG. 2. Two rows of four protrusions 58 act as surfaces for collection of fugitive aerosol mist and act to block and break up bubbles and foam. The top of the upper row of protrusions 58 may be coated with an antifoaming agent 59 as a last measure to prevent liquid from reaching the host instrument. The remoteness of antifoaming agent 59 allows it to be consumed only in extreme cases, thereby tube 51 typically provides protection for multiple uses. A passage must be left through expansion tube 51 for passage of a purge needle from the host instrument.

FIG. 4 is an enlarged exploded perspective view of an expansion-chamber and jar sparging vessel Only the top end 12 of sample jar 11 is shown including threads 15 and rim 13 surrounding opening 14. O-ring gasket 60 seals between rim 13 and flange 55. Tail piece 56 goes through 0-ring gasket 60 and is inserted into jar opening 14. Connector 70 is slid over expansion chamber tube 51 and internal threads 74 are threaded onto jar threads 15 whereby connector flange 77 pushes down on tube flange 55 and compresses O-ring gasket 60.

In actual use, connector 70 and gasket 60 are attached to expansion chamber tube 51 and top end 52 is simply inserted into the compression fitting of a host purge and trap instrument. The purge needle of the host instrument will protrude in plain view out of the bottom of connector 70. Cap 20 and septum 30 are removed from field sample jar 11 and discarded. Without pause, the full field sample jar 11 is attached to expansion chamber tube 51 by screwing connector 70 to jar 11. Purge and trap analysis then proceeds in a normal manner.

Returning once more to FIG. 1, a spike port 80 has been added to the bottom end 18 of common VOA jar 11. Spike port generally comprises passageway 82 having an inner end 83 and an outer end 84 providing for fluid communication to the interior of jar 11. A resilient cover, such as spike septum 87, blocks passageway 82 at outer end 84. Spike septum 87 may be similar to vial top septum 30 and is made of inert resilient material that will not interact with the sample, such as an inert elastomer or an elastomer encapsulated in an inert material, such as a solid fluorocarbon such as teflon. A commonly available septum has a inner layer 88 of teflon, for contacting the sample and an outer layer 89 of elastomer for elasticity and resiliency.

Retaining means for retaining spike septum 87 in passage blockage position includes external threads 85 around passageway 82 for attachment of cap 90. Cap 90 is similar to cap 20 and has an inner end 92 having internal threads 93 for attachment to passageway threads 85. Cap top 95 includes an inward flange 96 surrounding bore 98 for contacting and retaining septum 87 over passageway 82. A spiking needle can be passed through septum 87 to inject the spiking element into the sample.

Having described the invention, it can be seen that it provides a very convenient device for allowing a water sample to be analyzed directly from its collection bottle, thereby eliminating the loss of volatiles due to the transfer step. In addition the invention contains an expansion chamber with surface modifications for abating liquid passage dangers.

Although a particular embodiment of the invention has been illustrated and described, various changes may be made in the form, composition, construction, and arrangement of the parts without sacrificing any of its advantages. Therefore, it is to be understood that all matter herein is to be interpreted and illustrative and not in any limiting sense and it is intended to cover in the appended claims such modifications as come within the true spirit and scope of the invention.

I claim:

1. A sparger vessel for use with a purge and trap instrument; the instrument having a compression fitting; said vessel comprising:
    a jar for holding a sample to be tested; said jar having
        a top end including:
            a top opening;
            a rim surrounding said top opening; and
            external threads;
    an expansion chamber tube of transparent material having:
        a top end adapted for gas tight fit in a compression fitting of a host purge and trap instrument;
        a bottom end including an external flange; and
        an internal passage for fluid communication between said jar top opening and the host instrument;
    connector means for connecting said jar to said expansion chamber tube bottom end; said connector means comprising a tube having:
        a bottom end having internal threads for mating with said jar external threads; and
        a top end having an internal flange for bearing down on said expansion chamber tube bottom end external flange; and
    gasket means for forming a positive pressure seal between said expansion chamber tube bottom end and said jar.

2. A sparger vessel for use with a purge and trap instrument; the instrument having a compression fitting; said vessel comprising:
    a jar for holding a sample to be tested; said jar having
        a top end including a top opening;
    an expansion chamber tube of transparent material having:
        a top end adapted for gas tight fit in a compression fitting of a host purge and trap instrument;
        a bottom end including tail piece means for fitting just inside said jar top end opening; and
        an internal passage for fluid communication between said jar top opening and the host instrument;
    connector means for connecting said jar to said expansion chamber tube bottom end; and
    gasket means for forming a positive pressure seal between said expansion chamber tube bottom end and said jar.

3. A sparger vessel for use with a purge and trap instrument; the instrument having a compression fitting; said vessel comprising:
    a jar for holding a sample to be tested; said jar having
        a top end including a top opening;
    an expansion chamber tube of transparent material having:
        a top end adapted for gas tight fit in a compression fitting of a host purge and trap instrument;
        a bottom end; and
        an internal passage for fluid communication between said jar top opening and the host instrument; said expansion chamber tube internal passage including a plurality of protrusions;
    connector means for connecting said jar to said expansion chamber tube bottom end; and
    gasket means for forming a positive pressure seal between said expansion chamber tube bottom end and said jar.

4. The sparger vessel of claim 3 wherein:
    said expansion chamber interval passage includes a plurality of rows of protrusions.

5. A sparger vessel for use with a purge and trap instrument, the instrument having a compression fitting; said vessel comprising:
    a jar for holding a sample to be tested; said jar having:
        a top end including:
            a top opening;
            a rim surrounding said top opening; and
            external threads;
    an expansion chamber tube of transparent material having:
        a top end adapted for gas tight fit in a compression fitting of a host purge and trap instrument;
        a bottom end including:
            an external flange; and
            tail piece means for fitting just inside said jar top end opening; and
        an internal passage for fluid communication between said jar top opening and the host instrument;
    connector means for connecting said jar to said expansion chamber tube bottom end; said connector means comprising a tube having:
        a bottom end having internal threads for mating with said jar external threads; and
        a top end having an internal flange for bearing down on said expansion chamber tube bottom end external flange; and
    gasket means for forming a positive pressure seal between said expansion chamber tube bottom end and said jar.

6. The sparger vessel of claim 5 wherein:
    said jar includes:
        spiking port means for introducing a spike sample into a test sample while said expansion chamber top end is connected to a host instrument.

7. The sparger vessel of claim 6 wherein:
    said spiking port means includes:
        a passageway;
        a resilient septum blocking said passageway for retaining a sample and for allowing passage through said septum of a spiking needle; and
        retaining means for retaining said septum in position blocking said passageway while simultaneously providing spiking needle access to said septum.

8. The sparger vessel of claim 7 wherein:
    said retaining means includes:
        cap retaining threads on said jar external to said passageway; and a cap comprising a tube having:
  a first end having internal threads for mating with said passageway external threads; and
  a top end having:
    an internal flange for contacting and retaining said spiking septum to said jar.

9. An expansion chamber device for attachment to a purge and trap instrument, the instrument having a compression fitting and to a sample vial so that a sample can be purged without removal from the sample vial; said device comprising:
  an expansion chamber tube of transparent material having:
    a top end adapted for gas tight fit in a compression fitting of a host purge and trap instrument;
    a bottom end including:
      an external flange; and
      an internal passage for fluid communication between the vial top opening and the host instrument;
  connector means for connecting said expansion chamber tube bottom end to a field sample vial; said connector means comprising a tube having:
    a bottom end having internal threads for mating with external threads on a sample vial; and
    a top end having an internal flange for bearing down on said expansion chamber tube bottom end external flange; and
  gasket means for forming a positive pressure seal between said expansion chamber tube bottom end and the sample vial.

10. The expansion chamber device of claim 9 wherein:
  said expansion chamber tube bottom end further includes:
    tail piece means for fitting just inside a sample vial top end opening.

11. The expansion chamber device of claim 9 wherein:
  said expansion chamber tube internal passage includes:
    surface modifications for breaking up bubbles.

12. The expansion chamber device of claim 9 wherein;
  said expansion chamber tube internal passage includes a plurality of protrusions.

13. The expansion chamber device of claim 9 wherein:
  said expansion chamber internal passage includes a plurality of rows of protrusions.

* * * * *